(12) United States Patent
Mullen et al.

(10) Patent No.: US 8,507,718 B2
(45) Date of Patent: Aug. 13, 2013

(54) KETOCARBOXYLIC ACIDS, METHODS OF MANUFACTURE AND USES THEREOF

(75) Inventors: Brian D. Mullen, Delano, MN (US); Cora M. Leibig, Maple Grove, MN (US); Leo E. Manzer, Wilmington, DE (US)

(73) Assignee: Segetis, Inc., Golden Valley, MN (US)

( * ) Notice: Subject to any disclaimer, the term of this patent is extended or adjusted under 35 U.S.C. 154(b) by 61 days.

(21) Appl. No.: 13/294,751

(22) Filed: Nov. 11, 2011

(65) Prior Publication Data

US 2012/0123147 A1 May 17, 2012

Related U.S. Application Data

(60) Provisional application No. 61/412,590, filed on Nov. 11, 2010.

(51) Int. Cl.
*C07C 69/716* (2006.01)
*C07C 51/36* (2006.01)

(52) U.S. Cl.
USPC .......................................... 560/174; 562/400

(58) Field of Classification Search
USPC .......................................... 560/174; 562/400
See application file for complete search history.

(56) References Cited

U.S. PATENT DOCUMENTS

| | | | |
|---|---|---|---|
| 2,004,115 | A | 6/1935 | Izard et al. |
| 2,008,720 | A | 7/1935 | Lawson and Salzberg |
| 2,260,261 | A | 1/1940 | Morey |
| 2,556,135 | A | 6/1951 | Croxall et al. |
| 2,838,467 | A | 6/1958 | Dobay |
| 2,985,536 | A | 5/1961 | Stein et al. |
| 3,201,420 | A | 8/1965 | Fuzesi et al. |
| 3,963,800 | A | 6/1976 | Gipp et al. |
| 4,085,081 | A | 4/1978 | Heckles et al. |
| 4,792,411 | A | 12/1988 | Walsh |
| 5,095,098 | A | 3/1992 | McLain et al. |
| 5,202,413 | A | 4/1993 | Spinu |
| 5,552,513 | A | 9/1996 | Bhatia |
| 5,565,545 | A | 10/1996 | Kriesche et al. |
| 5,741,882 | A | 4/1998 | Fujii et al. |
| 5,917,059 | A | 6/1999 | Bruchmann et al. |
| 6,528,025 | B1 | 3/2003 | Boesch et al. |
| 6,806,392 | B2 | 10/2004 | Boesch et al. |
| 2003/0167681 | A1 | 9/2003 | Delgado Puche |
| 2003/0204042 | A1 | 10/2003 | Moethrath et al. |
| 2004/0024260 | A1 | 2/2004 | Winkler et al. |
| 2006/0069230 | A1 | 3/2006 | Papisov |
| 2010/0048940 | A1 | 2/2010 | Tulchinsky et al. |
| 2010/0216915 | A1 | 8/2010 | Bloom |
| 2010/0312006 | A1 | 12/2010 | Lake et al. |
| 2011/0021658 | A1 | 1/2011 | Selifonov |

FOREIGN PATENT DOCUMENTS

| | | |
|---|---|---|
| CN | 101020629 A | 8/2007 |
| DE | 1031512 | 6/1958 |
| FR | 1445013 | 7/1966 |
| JP | 28004327 | 9/1953 |
| JP | 2002348451 A | 12/2002 |
| WO | 2005097723 A2 | 10/2005 |
| WO | 2007062118 A2 | 5/2007 |
| WO | W02007/094922 A2 | 8/2007 |
| WO | 2009032905 A1 | 3/2009 |

OTHER PUBLICATIONS

Bechtold, et al., "Perfectly Alternating Copolymer of Lactic Acid and Ethylene Oxide as a Plasticizing Agent for Polylactide," Macromolecules 34: 8641-8648 (2001).

Burch, et al., "Synthesis of Cyclic Oligoesters and Their Rapid Polymerization to High Molecular Weight," Macromolecules 33: 5053-5064 (2000).

Carey, Francis A. and Sundberg, Richard J., Advanced Organic Chemistry, Second Edition, Part B: Reactions and Synthesis Plenum Press, NY (1983) p. 539-552.

Chopade, et al., "Acetalization of ethylene glycol with formaldehyde using cation-exchange resins as catalysts: batch versus reactive distillation," Reactive and Functional Polymers 34: 37-45 (1997).

Clarkson, et al., "Continuous Reactor Technology for Ketal Formation: An Improved Synthesis of Solketal," Organic Process Research & Development 5: 630-635 (2001).

Clerici, Angelo, et al., "Efficient Acetalisation of Aldehydes Catalyzed by Titanium Tetrachloride in a Basic Medium", Tetrahedron 54 (1998) p. 15679-15690.

Deutsch, et al., Investigations on heterogeneously catalysed condensations of glycerol to cyclic acetals, Journal of Catalysis 245: 428-435 (2007).

Gasparrini, F., "Synthesis of Dimethyl Acetals, Diethyl Acetals, and Cyclic Acetals Catalyzed by Aminopropylated Silica Gel Hydrocholoride(APSG-HCL)", Tetrahedron 40(9), (1984) p. 1491-1500.

Grajkowski, Andrzej et al., "Solid-Phase Synthesis of Thermolytic DNA Oligonucleotides Functionalized with a Single 4-Hydroxy-1-butyl or 4-Phosphato-/Thiophosphato-1-butyl Thiophosphate Protecting Group", J. Org. Chem, 2007, vol. 72, No. 3, 805-815.

Hiltunen, et al., Synthesis and Characterization of Lactic Acid Based Telechelic Prepolymers, Macromolecules 29: 8677-8682 (1996).

Hoydonckx, et al., "Esterification and transesterification of renewable chemicals," Topics in Catalysis 27(1-4): 83-96 (2004).

(Continued)

*Primary Examiner* — Johann R Richter
*Assistant Examiner* — Kofi Adzamli
(74) *Attorney, Agent, or Firm* — Cantor Colburn LLP

(57) ABSTRACT

Ketocarboxylic acids such as levulinic acid can be efficiently purified in high yield by esterification with a hydrocarbon polyol to the corresponding polyketocarboxylic ester, which can be readily purified, for example recrystallized. After purification, the ketocarboxylic ester can be hydrolyzed to provide pure ketocarboxylic acid, or a salt thereof, after removal of the esterifying hydrocarbon polyol, or used for other synthetic transformations. Advantageously, the polyketocarboxylic esters, ketocarboxylic acids, and salts thereof produced by this method are obtained in high purity.

35 Claims, No Drawings

(56) References Cited

OTHER PUBLICATIONS

Imwinkelried, et al., "Diisopropyl (2S,3S)-2,3-0-lsopropylidenetartrate [1,3-Dioxolane-4,5-dicarboxylic acid, 2,2-dimethyl-, bis(1-methylethyl)ester, (4R-trans)-]," Organic Syntheses 8: 201-230 (1993).

Transmittal and International Search Report for PCT/US2011/060451, mailed May 29, 2012, 8 pages.

Written Opinion of the International Searching Authority for PCT/US2011/060451, mailed May 29, 2012, 9 pages.

Kim, et al., "Preparation of High-Molecular-Weight Poly(L-lactic acid)-Based Polymers Through Direct Condensation Polymerization in Bulk State," Journal of Applied Polymer Science 100: 466-472 (2006).

Li, Tong-Shuang, et al., "Montmorillonite Clay Catalysis. Part 2. An Efficient and Convenient Procedure for the Preparation of Acetals Catalysed by Montmorillonite K-10," J. Chem Research (S) 26-27 (1997).

Meher, et al., "Technical aspects of biodiesel production by transesterification—a review," RSER 194: 1-21 (2004).

Meskens, Frans A. J., Methods for the Preparation of Acetals from Alcohols or Oxiranes and Carbonyl Compounds, Synthesisn (1981) 501-522.

Nagahata, et al., "Solid-Phase Thermal Polymerization of Macrocyclic Ethylene Terephthalate Dimer Using Various Transesterification Catalysts," Journal of Polyer Science: Part A: Polymer Chemistry 38: 3360-3368 (2000).

Nagata, et al., "Synthesis and Applications of [2-Methyl-2(oxoalkyl)-1,3-dioxolan-4-yl] methyl Acrylates for Photocrosslinking Agent," Osaka Kogyo Gijutsu Shikensho Kiho 37(1): 8-16 (1986).

Nakamura, et al., "Study on Ketalization Reaction of Poly (vinyl alcohol) by Ketones. IX. Kinetic Study on Acetalization and Ketalization Reaction of 1,3-Butanediol as a Model Compound for Poly (vinyl alcohol)," Polymer Science Part B: Polymer Physics 35(9): 1719-1731 (2000).

Newman, et al.,"Kinetic and Equilibrium Studies of Cyclic Ketal Formation and Hydrolysis," The Journal of the American Oil Chemist's Society 80: 6350-6355 (1958).

Otera, Junzo, Esterificaton, Methods, Reactions, and Applications, Wiley-VCH Verlag GmbH & Co., (2003) p. 1-19.

Pang, et al., "Review of conventional and novel polymerization processes for polyesters," Prog. Polym. Sci. 31: 1009-1037 (2006).

Pasto, D. J. and Serve, M. P., "Neighboring Group Participation by Carbonyl Oxygen", J. Amer. Chem. Soc., 87(7) (1965) 1515-1521.

Patel, et al., "Ketalization of ketones with diols catalyzed by metal (IV) phosphates as solid acid catalysts," Journal of Molecular Catalysis A: Chemical 194: 267-271 (2003).

Piantadosi, et al., "The Preparation of Cyclic Glycerol Acetals by Transacetalation," Journal of the American Chemical Society 80: 6613-6617 (1958).

Showier, et al., "Condensation Products of Glycerol with Aldehydes and Ketones. 2-Substituted m-Dioxan-5-OLS and 1,3-dioxolane-4-methanols," Chem. Rev. 67: 427-440 (1967).

Smith, et al., "The gem-Dialkyl Effect. III. Kinetic and Equilibrium Studies of Steroid Cyclic Ketal Formation and Hydrolysis," Journal of the American Chemical Society 90(5): 1253-1257 (1968).

Sodergard, et al., "Properties of lactic acid based polymers and their correlation with composition," Prog. Polym. Sci. 27: 1123-1163 (2002).

Vermylen, et al., "Study of the Thermal Evolution of the Cyclic-Oligomer Formation in a Cyclic-Oligomer-Free PET," Journal of Polymer Science: Part A: Polymer Chemistry 38: 416-422 (2000).

Wang, et al., "An efficient procedure for protection of carbonyls catalyzed by sulfamic acid," Journal of Molecular Catalysis A: Chemical 233: 121-126 (2005).

Wood, et al., "Cyclic polyesters: 1. Preparation by a new synthetic method, using polymer-supported reagants," Polymer 34(14): 3052-3058 (1993).

Xu, et al., "The monoblocking of symmetrical diketones on insoluble polymer supports," Can. J. Chem. 61: 1405-1409 (1983).

Yamada, Tatsuhiko et al., "Characterization of the products resulting from ethylene glycol liquefaction of cellulose", J. Wood Sci. 2001, vol. 47, 458-464.

Carey, M.A., et al., "Rapid Method for Measuring the Hydroxyl Content of Polyurethane Polyols" (published on the internet at http://www.polyurethane.org/s_api/doc_paper.asp?CE)=::1044 &DID=4060, accessed on Dec. 29, 2011.) 11 pages.

Hachihama, Yoshikazu; Hayashi, Izumi, "Studies on the Preparation of Plasticizers from Carbohydrate Sources ", Technology Reports of the Osaka University (1953), 3, 191-200.

International Preliminary Report on Patentability for PCT/US2011/060451 mailed May 23, 2013, 11 pages.

KETOCARBOXYLIC ACIDS, METHODS OF MANUFACTURE AND USES THEREOF

CROSS-REFERENCE TO RELATED APPLICATION

This application claims the benefit of U.S. Provisional Application Ser. No. 61/412,590, filed Nov. 11, 2010, the entire contents of which are incorporated by reference herein.

BACKGROUND

This disclosure relates to ketocarboxylic acids and ketocarboxylic esters, methods of manufacture and uses thereof. In particular, this disclosure relates to the purification of compositions of ketocarboxylic acids and the intermediates produced thereby.

Ketocarboxylic acids are used in the manufacture of ketocarboxylic esters. Both ketocarboxylic acids and ketocarboxylic esters can be used as additives or in the manufacture of ketal adducts. The ketal adducts can be used as plasticizers in polymers and can also be used to synthesize polyamides, polyurethanes, polyesters, and other polymers.

SUMMARY

The inventors hereof have discovered methods for the production of ketocarboxylic acid compositions that can have low levels of impurities and that can be used to manufacture products, for example ketocarboxylic esters, polymers, and plasticizers amongst other products, that are not contaminated with byproducts from the manufacture of the ketocarboxylic acids by acid hydrolysis of furfuryl alcohol, starch, or cellulose.

Accordingly, disclosed herein is a method for reducing a content of an impurity in a ketocarboxylic acid composition comprising at least 1 wt % of the impurity and a ketocarboxylic acid I

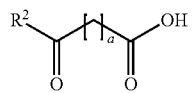
I wherein $R^2$ is $C_1$-$C_6$ alkyl and a=0-3, the method comprising contacting a hydrocarbon polyol II G-[OH]$_t$    II wherein G is a hydrocarbyl group having a valence of t, and t=2-3, with the ketocarboxylic acid composition in an esterification reaction mixture wherein the ketocarboxylic acid I is present in an amount of at least 0.75 equivalents of the ketocarboxylic acid I per one equivalent of hydroxy group in the hydrocarbon polyol II, under conditions effective to form a ketocarboxylic ester III

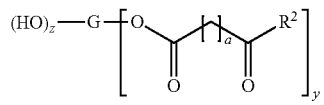
III wherein $R^2$ is $C_1$-$C_6$ alkyl, a=0-3, y=2-3 and z=0-1, provided that z+y=t; and isolating the ketocarboxylic ester III from the esterification reaction mixture.

Also disclosed herein is a method for the purification of a composition comprising ketocarboxylic acid I and an impurity,

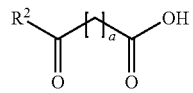
I wherein $R^2$ is $C_1$-$C_6$ alkyl, and a=0-3, the method comprising esterifying a hydrocarbon polyol II G-[OH]$_t$    II wherein G is an ethylene, n-butylene or n-hexylene having a valence of t, and t=2, with a composition comprising an impurity and the ketocarboxylic acid I in an esterification reaction mixture, wherein the ketocarboxylic acid I is present in the esterification reaction mixture in an amount of at least 0.75 equivalents of the ketocarboxylic acid I per one equivalent of hydroxy group in the hydrocarbon polyol II, to form a ketocarboxylic ester III

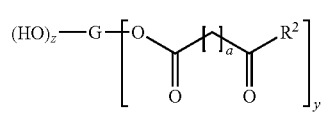
III wherein $R^2$ is $C_1$-$C_6$ alkyl, a=0-3, y=2-3, and z=0-1, provided that z+y=t; isolating the polyketocarboxy ester III from the esterification reaction mixture; and decomposing the isolated ketocarboxylic ester III to provide the purified ketocarboxylic acid I composition or a salt thereof.

Disclosed herein too is a ketocarboxylic ester composition comprising a polyketocarboxylic acid III

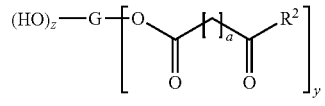
III wherein $R^2$ is $C_1$-$C_6$ alkyl, a=0-3, y=2-3 and z=0-1, provided that z+y=t; and a residue of a biomass.

Also disclosed herein is a purified ketocarboxylic ester composition comprising at least 99 wt % of a ketocarboxylic acid III

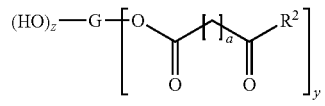
III wherein $R^2$ is $C_1$-$C_6$ alkyl, a=0-3, y=2-3 and z=0-1, provided that z+y=t; and up to 1 wt % of an impurity, based on the total weight of the purified ketocarboxylic acid composition.

Also disclosed herein is a composition comprising at least 99 wt % of a polyketocarboxy ester having the formula IIIa

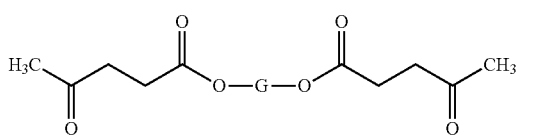

IIIa wherein G is ethylene, n-propylene, n-butylene, or hexylene; and up to 1 wt % of an impurity.

Also disclosed herein is a mono-ester compound having the formula

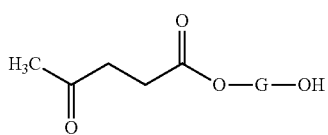

wherein G is ethylene, n-propylene, n-butylene, or n-hexylene.

Also disclosed herein is a purified composition comprising at least 99 wt % of a ketocarboxylic acid I

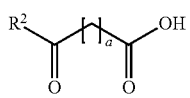

I wherein $R^2$ is $C_1$-$C_6$ alkyl, and a=0-3; and up to 1 wt % of an impurity, based on the total weight of the purified ketocarboxylic acid composition.

DETAILED DESCRIPTION

Commercially available ketocarboxylic acids are contaminated with impurities, primarily byproducts from the acid degradation of furfuryl alcohol, starch, or cellulose to produce the ketocarboxylic acids. Such impurities include angelica lactones, furanics, aldehydes, and various oligomers. When used in the manufacture of ketocarboxylic esters or other adducts, the presence of impurities results in colored products, and/or products having a limited shelf life.

The inventors hereof have found that ketocarboxylic acids such as levulinic acid can be efficiently purified in high yield by esterification with a hydrocarbon polyol to the corresponding polyketocarboxylic ester, which can be readily recrystallized. After recrystallization, the ketocarboxylic ester can be hydrolyzed to provide pure ketocarboxylic acid, or a salt thereof, after removal of the esterifying hydrocarbon polyol, or used for other synthetic transformations. Advantageously, the polyketocarboxylic esters, ketocarboxylic acids, and salts thereof produced by this method are obtained in high purity. In particular, the polyketocarboxylic esters, ketocarboxylic acids, and salts thereof, have little or no oligomeric impurities, low levels of aldehydes, low levels of sulfur-containing acid impurities, low levels of transition metal impurities, and low color.

In another particularly advantageous aspect of the method, one or both of the hydrocarbon polyol and the ketocarboxylic acid are biosourced. Biosourced ketocarboxylic acids can be contaminated with a variety of byproducts arising from their production. The methods described herein are effective to purify ketocarboxylic acid compositions comprising 0.1-10 wt %, 1-10 wt %, or 1-8 wt % of contaminants. The methods are also effective when the ketocarboxylic acid compositions are wet, that is, containing 1 wt %, 5 wt %, 10 wt %, 30 wt %, or up to 50 wt % of water.

The method for the purification of a ketocarboxylic acid I comprises esterifying hydrocarbon polyol II with the ketocarboxylic acid I in an esterification reaction mixture G-[OH]$_t$     II wherein G is a hydrocarbyl group having a valence of t. In an embodiment, G is a $C_2$-$C_{32}$ hydrocarbon containing 1 or more straight chain, branched or cyclic groups that can be saturated, unsaturated, aromatic, or substituted with up to 12 ether oxygens; specifically, G is a $C_2$-$C_{12}$ alkylene, $C_5$-$C_8$ cycloalkylene, or $C_6$-$C_{12}$ arylene, optionally substituted with up to 5 ether oxygens; more specifically, G is a $C_2$-$C_{12}$ alkylene optionally substituted with up to 5 ether oxygens; a $C_2$-$C_6$ alkylene; and still more specifically, G is ethylene, n-propylene, n-butylene, or n-hexylene. In an embodiment, the number of hydroxyl groups, t, is 1-10, specifically 2-8, more specifically 2-6, still more specifically 2-4, and still more specifically 2-3 or 2. For example, hydrocarbon polyol II can be a triol or diol wherein G is a $C_2$-$C_{12}$ alkylene, specifically ethylene, n-propylene, n-butylene, or n-hexylene. In some embodiments a mixture of polyols can be used wherein G and t are different, or a mixture of polyols can be used wherein G is different but t is the same, for example 2 or 3. For example, a composition comprising fatty diols and triols (e.g., $C_8$-$C_{28}$ aliphatic alcohols, for example $C_{12}$-$C_{18}$, or $C_{14}$-$C_{16}$ aliphatic alcohols) can be used.

Hydrocarbon polyol II is contacted with 0.75, 1, 1.2, 4, 5, 6, more equivalents of the ketocarboxylic acid to be purified, in particular ketocarboxylic acid I

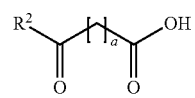

I in an esterification reaction mixture under conditions effective to form a ketocarboxylic ester III. In formula I, $R^2$ is $C_1$-$C_6$ alkyl, specifically a $C_1$-$C_3$ alkyl, more specifically a $C_1$-$C_2$ alkyl, and still more specifically methyl. Further in formula I, a is 0-3, more specifically 1-2, and still more specifically 2. When a is 0, a single bond connects the two carbonyl groups. The hydrocarbon polyol II is contacted with at least 0.75 equivalents of the ketocarboxylic acid I (per one equivalent of hydroxy group in the hydrocarbon polyol II).

Esterification occurs in the presence of no added catalyst (the ketocarboxylic acid I can function as a catalyst), or an acid catalyst. Esterification produces a ketocarboxylic ester III

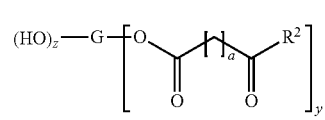

III wherein $R^2$ and a are the same as in the ketocarboxylic acid I, t is the valence of hydrocarbon polyol II, y is 1-10, z is 0-9, and y+z=t. The degree of esterification can be controlled by controlling various reaction parameters such as the ratio of the ketocarboxylic acid I to the polyol II, the catalyst type, the catalyst concentration, removal of water, temperature or pressure. Alternatively, for example, use of relatively lower equivalents of ketocarboxylic ester results in less esterification (y<z), whereas relatively higher amounts of ketocarboxylic ester results in higher esterification (y>z), or z=0.

Ketocarboxylic ester III, for example, a diketocarboxylic ester, can be readily isolated from the esterification reaction mixture by crystallization, or alternatively isolated by other methods, and subsequently recrystallized. Subsequent recrystallization(s) can provide compound III of even higher purity. Other methods of isolating the ketocarboxylic ester include washing, crystallizing, filtering, liquid-liquid phase separating, precipitation, or a combination of at least one of the foregoing. The ketocarboxylic ester III can then be used for further reaction or as a product, for example a polymer additive.

In a specific embodiment the ketocarboxylic ester III is decomposed to provide the purified ketocarboxylic acid I

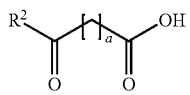

wherein $R^2$ and a are as defined above, or a salt thereof.

In a specific embodiment, with reference to each of formulas I, II, and III,
  G is a $C_2$-$C_{12}$ alkylene, $C_5$-$C_8$ cycloalkylene, or $C_6$-$C_{12}$ arylene, optionally substituted with up to 5 ether oxygens;
  $R^2$ is $C_1$-$C_6$ alkyl,
  a=0-3, y=2-3, and z=0.

In another specific embodiment, with reference to each of formulas I, II, and III,
  G is a $C_2$-$C_{12}$ alkylene optionally substituted with up to 5 ether oxygens,
  $R^2$ is $C_1$-$C_3$ alkyl,
  a=1-2, y=2, and z=0.

In another specific embodiment, with reference to each of formulas I, II, and III,
  G is a $C_2$-$C_6$ alkylene
  $R^2$ is methyl,
  a=1-2, y=2 and z=0.
  G is n-butylene,
  $R^2$ is methyl,
  a=2, y=2, and z=0.

In a more specific embodiment, at least 0.75, 1, 1.2, 3, 4, 5, 6, or more equivalents of ketocarboxylic acid Ia (levulinic acid)

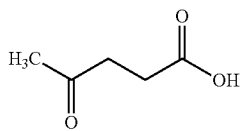

containing an impurity are contacted by an alkylene diol of the formula IIa

wherein G is a $C_1$-$C_{10}$ alkylene, specifically a $C_1$-$C_6$ alkylene, and more specifically, ethylene, n-propylene, n-butylene, or n-hexylene, in the presence or absence of an esterification catalyst, to produce a diketocarboxylic ester IIIa

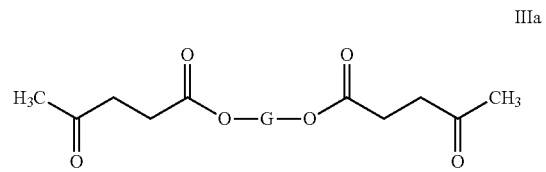

wherein G is as defined in formula IIa. Diketocarboxylic ester IIIa can be readily isolated from the esterification mixture by crystallization, or alternatively isolated by other methods, and subsequently recrystallized. Subsequent recrystallization(s) can provide compound IIIa of even higher purity. The diketocarboxylic ester IIIa can then be used for further reaction, or decomposed to provide the purified ketocarboxylic acid Ia after removal of the hydrocarbyl diol IIa.

In an embodiment, ketocarboxylic ester III can be decomposed to form a mono-ester having the structure (IV)

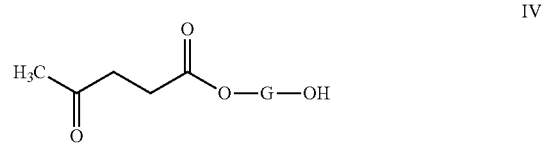

wherein G is a hydrocarbyl group having a valence of 2, specifically ethylene, n-propylene, n-butylene, or n-hexylene. In an aspect of the embodiment, the mono-ester is present in an amount of up to 20 wt % and further comprises levulinic acid in an amount of up to 30 wt %, based on the total weight of the composition. In another embodiment, the ketocarboxylic ester III is decomposed to provide purified levulinic acid.

In particular, in one method of manufacturing the ketocarboxylic ester III, the hydrocarbon polyol II along with at least 0.75 equivalents of the ketocarboxylic acid I (per one equivalent of hydroxy group in the hydrocarbon polyol II) and an acid catalyst are charged to a reactor. In an embodiment, the ratio of equivalents of the ketocarboxylic acid I to the equivalents of hydroxy group in the hydrocarbon polyol II is greater than or equal to about 0.75:1, specifically greater than or equal to about 0.85:1 and more specifically greater than or equal to about 1:1. In an embodiment, 0.75 to 2 equivalent of the ketocarboxylic acid I are used, specifically 1.0 to 1.75 equivalents of ketocarboxylic acid I per one equivalent of hydroxy moieties in the hydrocarbon polyol II.

The esterification and/or ketalization is conducted in the presence of an acid catalyst, which can be either a Lewis or Brønsted-Lowry acid. Acid catalysts that are known homogeneous catalysts for either ketal formation or esterification or transesterification reactions can be used, for example strong protic acid catalysts, e.g., Brønsted-Lowry acids that have a Ka of 55 or greater. Examples of strong protic acid catalysts include sulfuric acid, arylsulfonic acids, and hydrates thereof such as p-toluenesulfonic acid monohydrate, methane sulfonic acid, camphor sulfonic acid, dodecyl benzene sulfonic acid, perchloric acid, hydrobromic acid, hydrochloric acid, 2-naphthalene sulfonic acid, and 3-naphthalene sulfonic acid. In other embodiments, weak protic acid catalysts, e.g., having a Ka of less than 55, can be used, for example phosphoric acid, orthophosphoric acid, polyphosphoric acid, and sulfamic acid. Aprotic (Lewis acid) catalysts can include, for example, titanium tetraalkoxides, aluminum trialkoxides, tin II alkoxides, carboxylates, organo-tin alkoxides, organo-tin carboxylates, and boron trifluoride. A combination comprising any one or more of the foregoing acid catalysts can be used. In some embodiments, the method employs a substantially nonvolatile acid catalyst such that the acid does not transfer into the distillate, such as sulfuric or sulfamic acid. In an exemplary embodiment, the homogenous catalyst is camphor sulfonic acid.

Instead of, or in addition to the homogenous acid catalyst, a heterogenous acid catalyst can be used, where the acid catalyst is incorporated into, onto, or covalently bound to, a solid support material such as resin beads, membranes, porous carbon particles, zeolite materials, and other solid supports. Many commercially available resin-based acid catalysts are sold as ion exchange resins. One type of useful ion exchange resin is a sulfonated polystyrene/divinyl benzene resin, which supplies active sulfonic acid groups. Other commercial ion exchange resins include LEWATIT® ion exchange resins sold by the Lanxess Company of Pittsburgh, Pa.; DOWEX™ ion exchange resins sold by the Dow Company of Midland, Mich.; and AMBERLITE® and AMBERLYST® ion exchange resins sold by the Dow Company of Midland, Mich. In embodiments, AMBERLYST® 15, AMBERLYST® 35, AMBERLYST® 70 are used. In these embodiments, the resin-based catalyst is washed with water, and subsequently, an alcohol, such as methanol or ethanol, and then dried prior to use. Alternatively, the resin is not washed before its first use. In embodiments, Nafion® resins (from DuPont in Wilmington, Del.) can also be used as heterogeneous catalysts in neat form or filled with silica. In use, the heterogenous catalysts are added to a reaction mixture, thereby providing a nonvolatile source of acid protons for catalyzing the reactions. The heterogenous catalysts can be packed into columns and the reactions carried out therein. As the reagents elute through the column, the reaction is catalyzed and the eluted products are free of acid. In other embodiments, the heterogeneous catalyst is slurried in a pot containing the reagents, the reaction is carried out, and the resulting reaction products filtered or distilled directly from the resin, leaving an acid-free material.

The amount of acid catalyst is about 2 to 20,000 parts per million (ppm), specifically about 10 to about 10,000 ppm, specifically about 20 to about 5000 ppm, and more specifically about 30 to about 2500 ppm, relative to the total weight of the reactants. In this case, the reactants are the sum of hydrocarbon polyol II and the at least 0.75 or more equivalents of a ketocarboxylic acid III (per 1 equivalent of hydroxy groups in the hydrocarbon polyol II).

When camphor sulfonic acid is used as the acid catalyst to produce the ketocarboxylic ester III, it is used in amounts of about 5 to 5,000 parts per million (ppm), specifically about 10 to about 1000 ppm, specifically about 15 to about 800 ppm, and more specifically about 20 to about 600 ppm, relative to the total weight of the reactants. In this case, the reactants are the sum of hydrocarbon polyol II and the at least 0.75 or more equivalents of a ketocarboxylic acid I.

The acid catalyst can be charged directly into the reactant mixture comprising the hydrocarbon polyol II and the ketocarboxylic acid I or alternatively it can be diluted in water or one of the reactants prior to being charged into the reactant mixture. The acid catalyst can be diluted to about 0.01N to about 5N, specifically about 0.1N to about 4N, and more specifically about 0.5N to about 3N prior to introduction into the reactant mixture. The dilute acid catalyst can be continuously added to the reactant mixture throughout the course of the reaction or alternatively it can be added instantaneously to the reactant mixture in a single charge.

In an embodiment, in one method of manufacturing the ketocarboxylic acid, the hydrocarbon polyol II and at least 0.75 or more equivalents of a ketocarboxylic acid I (per 1 equivalent of hydroxy groups in the hydrocarbon polyol II) are charged to the reactor. The reaction to produce the ketocarboxylic ester III can be conducted in either a batch reactor, a continuous reactor or in a semicontinuous reactor. It is desirable for the reactor to have heating, cooling, agitation, condensation, and distillation facilities.

In an embodiment, the batch reactor for producing the ketocarboxylic acid can comprise a single continuous stirred tank reactor in fluid communication with a reboiler that is fitted with a distillation column. In another embodiment, the system (not shown) for producing the ketocarboxylic acid can comprise a single continuous stirred tank reactor that is fitted with a distillation column. The distillation column is used to remove excess reactants and to distill the water condensate from the reaction. In another embodiment, the distillation column is used to remove water from the esterification reaction mixture during at least a portion of the contacting or esterifying. In another embodiment, there is less than or equal to a 20 wt % percent loss of 1,4-butanediol as tetrahydrofuran, more specifically 10 wt %, in a water stream during distillation before, during or after isolating or decomposing the reaction mixture.

In a batch reactor, the reactants and catalyst are charged to the reactor in batches and the product is extracted from the reactor in batches only after the reaction has been completed to an extent of about 80% or more. While a batch reactor can be used to react the reactants under a variety of different conditions, it is desirable to use a batch reactor when the product is manufactured by introducing the acid catalyst into the reactor in one charge. An exemplary batch reactor is a stainless steel or Hastelloy-type reactor. An example of a batch reactor is a continuous stirred tank reactor. It is desirable for the batch reactor to be equipped with distillation facilities for further purification of the product. The reaction to produce the ketocarboxylic acid can be conducted in a single reactor or in plurality of batch reactors. In an embodiment, the esterification can be conducted in a first batch reactor, while the hydrolysis of the ketocarboxylic ester III to produce pure ketocarboxylic acid can be conducted in the same or in a second batch reactor.

In a continuous reactor system the reactants are charged to a first reactor. When the conversion of reactants to products is measured to be greater than or equal to about 50%, a portion of the product mixture from the first reactor is subjected to additional finishing processes in a second reactor, while at the same time additional reactants and catalyst are continuously being charged to the first reactor to be converted into the ketocarboxylic ester III. A continuous reactor system generally employs a plurality of reactors in series or in parallel so that various parts of the process can be conducted in different reactors simultaneously.

In an embodiment, the reactor comprises a plurality of reactors (e.g., a multistage reactor system) that are in fluid communication with one another in series or in parallel. The plurality of reactors are used to react the hydrocarbon polyol II with the ketocarboxylic acid I, to recycle the reactants and to remove unwanted byproducts and impurities so as to obtain a ketocarboxylic ester III that is stable and has a long shelf life. In an embodiment, a portion of the plurality of reactors can be used primarily to react reactants to manufacture the ketocarboxylic ester III, while another portion of the plurality of reactors can be used primarily to isolate the ketocarboxylic ester III and yet another portion of the plurality of reactors can be used to hydrolyze the ketocarboxylic ester III or to remove the residual catalyst and other byproducts that can hamper the formation of a stable product that has good shelf stability.

In an exemplary embodiment, the esterification of the hydrocarbon polyol II with at least 0.75 or more equivalents of a ketocarboxylic acid I (per 1 equivalent of hydroxy groups in the hydrocarbon polyol II) to produce a ketocarboxylic ester III is conducted in a first batch reactor. In one method of manufacturing the ketocarboxylic ester III, a hydrocarbon polyol II and the ketocarboxylic acid I are charged to the first batch reactor along with the acid catalyst. The contents of the first batch reactor are heated while being subjected to agitation. Volatile reactants or byproducts are collected in a condenser that is in fluid communication with the first batch reactor. The ketocarboxylic ester III can be isolated from unreacted reactants and other reaction byproducts prior to the hydrolysis to produce the ketocarboxylic acid. In an embodiment, the ketocarboxylic ester III is isolated via crystallization or distillation.

The ketocarboxylic ester III can then be used as an intermediate in other chemical syntheses, or as a product, for example as a polymer additive. Advantageously, the ketocarboxylic ester III is hydrolyzed with water to produce the purified ketocarboxylic acid I. During the hydrolysis, excess hydrocarbon polyol I is removed from the ketocarboxylic acid by distillation.

In an embodiment, the first batch reactor is heated to a temperature of about 80 to about 250° C., specifically about 90 to about 230° C., and specifically about 100 to about 210° C. to facilitate the esterification of the hydrocarbon polyol II by the ketocarboxylic acid I. The esterification can be carried out under a blanket of an inert gas (e.g., argon, nitrogen, and the like) or alternatively can be carried out in a vacuum (i.e., sub-atmospheric pressure). The first batch reactor can be subjected to a vacuum of 5 to about 500 torr, specifically about 10 to about 100 torr.

Upon completion of the esterification in the first batch reactor, the reaction solution is cooled down to crystallize the ketocarboxylic ester III. The crystalline ketocarboxylic ester III can then be washed in a first solvent to remove any contaminants. The washed ketocarboxylic ester III can then be redissolved in a second solvent and recrystallized to produce a pure form of the ketocarboxylic ester III. The first and the second solvent can be the same or different. In an embodiment, the first solvent is water and the second solvent is water as well. Water also removes color bodies, acid catalyst and unreacted ketocarboxylic acid I from the reaction mixture. The water can contain some salt or dilute base.

The heating and cooling steps can be performed to conduct re-crystallization. The pure form of the ketocarboxylic ester III has a purity of greater than or equal to about 98%, specifically greater than or equal to about 99%, on a weight basis. The pure form of the ketocarboxylic ester III can comprise white, shiny spherical and needle-shaped crystals.

While water is used as the first and the second solvent for crystallizing the ketocarboxylic ester III, other organic solvents can also be used to crystallize it. Examples of other organic solvents are methanol, ethanol, acetone, benzene, toluene, diethyl ether, ethyl acetate, or the like, or a combination comprising at least one of the foregoing solvents.

In an embodiment, the pure form of the ketocarboxylic ester III is then hydrolyzed with water in a second batch reactor. The decomposition of ketocarboxylic ester III after purification to obtain the purified ketocarboxylic acid is conducted via hydrolysis with acid or via saponification with base.

In an embodiment, the purified ketocarboxylic acid is obtained via the hydrolysis of ketocarboxylic ester III with an acid catalyst. The acid catalyst decomposes the ketocarboxylic ester III to form a mixture of hydrocarbon polyol II and the ketocarboxylic acid I. Following the decomposition, the mixture of the hydrocarbon polyol II and the ketocarboxylic acid I is neutralized and filtered. Water is then stripped from the mixture and the purified ketocarboxylic acid and the hydrocarbon polyol are heated and distilled off from the mixture. During the distillation, tetrahydrofuran is present in an overhead water stream in an amount of less than or equal to about 50 weight percent. The ketocarboxylic acid obtained in this manner is highly purified and is purer than the ketocarboxylic acid I that is used to produce the ketocarboxylic ester III. In another aspect of the embodiment, there is less than or equal to a 20 weight percent loss of 1,4-butanediol as tetrahydrofuran in a water stream during distillation before, during or after the decomposing the reaction mixture.

In order to decompose the ketocarboxylic ester III, it is charged to a reactor with an excess of water and a catalytic amount of the acid. The reactor can be the first reactor or the second reactor. The acid catalysts can be similar to those used to catalyze the reaction between the hydrocarbon polyol II and the ketocarboxylic acid I to yield the ketocarboxylic ester III. Examples of mineral acids are hydrochloric acid, sulfuric acid, and para-toluene sulfonic acid. An exemplary acid catalyst is sulfuric acid.

The batch reactor is subjected to agitation and is heated to reflux for about 2 to about 8 hours at a temperature of about 60 to about 150° C., specifically about 70 to about 90° C. to decompose the ketocarboxylic ester III. Following the decomposition, the reaction mixture is neutralized to quench any reversible reactions that lead to the reformation of the ketocarboxylic ester III. The reaction mixture is then filtered.

Neutralization is conducted with a base such as mono or di-basic sodium or potassium phosphates, mono, di- or tri-basic calcium or zinc phosphate, barium carbonate, barium phosphate, zinc carbonate, sodium carbonate, potassium carbonate, sodium citrate, potassium citrate, calcium citrate, basic alumina, a weakly basic anion exchange resin, and the like. In an embodiment, the aforementioned bases can be in the form of a bed. The ketocarboxylic acid can contact the bed either in a single pass or in multiple passes. Filtration is conducted following neutralization to remove un-neutralized acid catalyst and to remove salts formed as a result of the neutralization. In an embodiment, filtration can be conducted in a packed bed of CELITE® under pressure.

The filtered mixture of the hydrocarbon polyol and the ketocarboxylic acid is heated to remove the water. In order to remove the water, the filtered mixture is generally heated to a temperature around the boiling point of water specifically about 80 to about 100° C., with or without vacuum.

It is then subjected to distillation to strip off the hydrocarbon polyol from the ketocarboxylic acid. In an embodiment, the distillation is vacuum distillation, conducted at a vacuum of about 5 to about 10 ton. The ketocarboxylic acid thus obtained has a purity of greater than or equal to about 98%, specifically greater than or equal to about 99% and more specifically greater than or equal to about 99.5%, while displaying a yellowness index of less than 5 units as measured by ASTM E 313. Contaminants that are present in amounts of less than or equal to about 1 wt %, more specifically 0 to 1 wt, % are furfural, formic acid, furfuryl alcohol, hydroxymethyl furfural, angelica lactone, acetic acid, methanol and the like. In an embodiment the contaminant, or impurity, is a residue of a biomass. The residue of a biomass arises from the manufacture of the hydrocarbon polyols or ketocarboxylic acids from a biomass such as cellulose, lignocellulose, or other polysaccharides such as starches, inulin, and xylan.

In another embodiment, another method of decomposing the ketocarboxylic ester III comprises saponifying the ketocarboxylic ester III to form a mixture of hydrocarbon polyol II and the ketocarboxylic acid I, the ketocarboxylic ester III is mixed water and is heated to a temperature of about 40 to about 150° C., specifically about 70 to about 90° C., and more specifically about 75 to about 85° C., in the presence of an equivalent of a base catalyst. Additional base is then added to fully precipitate the ketocarboxylate salt from the reaction mixture. The precipitation of the ketocarboxylate salt using additional base is optional. The ketocarboxylate salt is then filtered away from the hydrocarbon polyol and re-acidified with an acid to form the ketocarboxylic acid and salt. The ketocarboxylic acid is stripped of water and the salt is filtered to obtain ketocarboxylic acid. The ketocarboxylic acid is then distilled to obtain purified ketocarboxylic acid.

The base catalyst can comprise an ammonium salts, hydroxides, and alkoxides. Examples of ammonium salts are quaternary ammonium hydroxides such as tetramethyl ammonium hydroxide, tetraethyl ammonium hydroxide, tetrapropyl ammonium hydroxide, tetrabutyl ammonium hydroxide, and tetraoctyl ammonium hydroxide. Examples of metal hydroxides are alkali metal hydroxides and alkaline earth metal hydroxides. Examples of alkali metal hydroxides are lithium hydroxide, sodium hydroxide, and potassium hydroxide. Examples of alkaline earth metal hydroxides are magnesium hydroxide and calcium hydroxide. Examples of alkoxides are lithium, sodium, and potassium alkoxides such as lithium methoxide, lithium ethoxide, lithium butoxide, sodium methoxide, sodium ethoxide, sodium butoxide, potassium methoxide, potassium ethoxide, and potassium butoxide. Combinations of these bases can also be used.

The base catalyst is added in amounts of about 1.5 to about 3 molar equivalents to the polyketocarboxylic acid.

In an embodiment, after the decomposition to produce the ketocarboxylic acid, additional base is added to the mixture to convert the ketocarboxylic acid to precipitate the ketocarboxylate salt. An exemplary additional base is sodium hydroxide.

Other bases listed above can also be used. The base can be added in an amount of about 0.8 to about 1.5 moles, specifically about 0.9 to about 1.3 moles, based on the total moles of the ketocarboxylic acid. Other anions for the ketocarboxylate salt are lithium, sodium, potassium, calcium, magnesium, ammonium and $NH_nR_{4-n}$, wherein R=alkyl, aryl, alkaryl, or arylalkyl and where n=0-4.

The filtration of the ketocarboxylic acid from the polyol is conducted via a pressurized filter that optionally contains CELITE®.

The ketocarboxylic salt is then re-acidified to form the ketocarboxylic acid. In an embodiment, the acid used for re-acidification of the ketocarboxylate salt is sulfuric acid. The sulfuric acid can be diluted with water prior to re-acidification. The sulfuric acid is present in the diluted sulfuric acid solution in an amount of about 5 to about 20 wt %, specifically about 7 to about 13 wt %, based on the amount of diluted sulfuric acid solution. Other acids listed above can also be used.

Water present in the ketocarboxylic acid is stripped off. Salt generated during the re-acidification can be filtered out. The ketocarboxylic acid is then optionally distilled under a vacuum of about 1 to about 10 Torr, specifically about 3 to about 7 Torr. The ketocarboxylic acid thus obtained has a purity of greater than or equal to about 98%, specifically greater than or equal to about 99% and more specifically greater than or equal to about 99.5%, while displaying a yellowness index of less than 20 units as measured by ASTM E 313, preferably less than 5 units as measured by ASTM E 313.

It is desirable for the ketocarboxylic acid to be of high purity. The pure form of the ketocarboxylic acid I obtained by the present method has a purity of greater than or equal to about 95%, specifically greater than or equal to about 98%, and more specifically greater than or equal to about 99%, on a weight basis.

In particular, it is desirable for the ketocarboxylic acid, in purified form, to have less than or equal to about 5 wt %, specifically less than or equal to about 1 wt %, more specifically less than or equal to about 0.5 wt %, based on the total weight of the ketocarboxylic acid I, of an oligomeric side product. "Oligomeric side products" as used herein are undesired impurities with or without repeat units and having a molecular weight higher than the molecular weight of the ketocarboxylic acid I.

The following examples, which are meant to be exemplary, not limiting, illustrate compositions and methods of manufacturing of some of the various embodiments described herein.

EXAMPLES

Example 1

LA-BDO-LA, from Crude LA

This example details the manufacture of diketone diester from a sample of commercially available crude levulinic acid (LA). Crude levulinic acid was examined using gas chromatography with a flame ionization detector (GC-FID). The composition was 94% pure and contained 0.5 wt % low molecular weight components (angelica lactones, furanics) and 5 wt % higher molecular weight impurities (oligomers of unknown composition). As shown in Scheme 1, this crude levulinic acid (a ketocarboxylic acid I wherein a=2) is reacted with a hydrocarbon polyol II (1,4-butanediol, BDO) to form the ketocarboxylic ester III (a diketone diester, LA-BDO-LA).

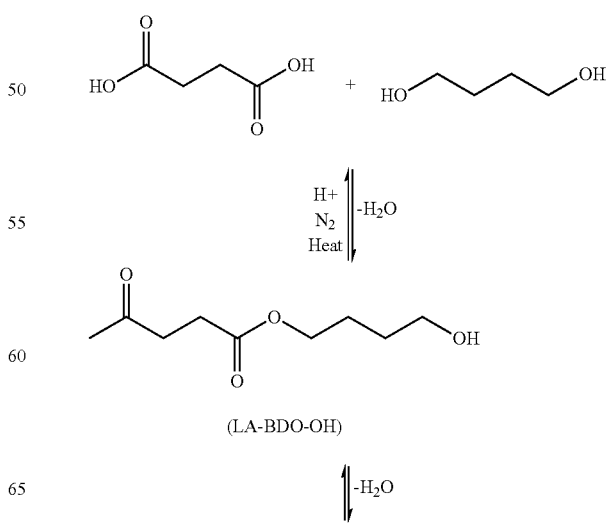

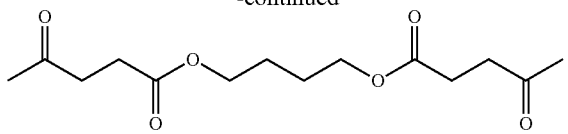

(LA-BDO-LA.)

Crude levulinic acid (29.05 g (0.25 mol) LA, 10.73 g (0.12 mol) 1,4-butanediol, and 200 ppm camphor sulfonic acid were added to an empty 500 mL, 3-neck round bottom flask equipped with a magnetic stir-bar, Dean-Stark trap and overhead condenser, a thermocouple, and a nitrogen inlet. The contents were heated with an oil bath for 6 hours at 160° C. Volatile condensate was collected in the Dean Stark trap. A sample of the reactor was analyzed by GC-FID and the composition was found to be as follows.

| | |
|---|---|
| 0.016% | un-reacted 1,4-BDO |
| 9.14% | un-reacted levulinic acid |
| 3.20% | LA-BDO-OH |
| 81.53% | LA-BDO-LA product |
| 6.11% | unknown higher molecular weight species |

The composition was crystallized by the addition of water to afford white crystals. The yield of crystals was 16.5 grams and the composition by GC-FID was found to be:

| | |
|---|---|
| 0.5% | LA-BDO-OH |
| 99.4% | LA-BDO-LA product |
| 0.1% | unknown higher molecular weight species |

Example 2

LA-BDO-LA, from Crude LA

A second sample of crude levulinic acid contained 10 wt % water, less than 1 wt % sodium salts, 88.3% levulinic acid, 0.26% angelica lactone and furanic impurities, and 0.45% oligomers of unknown composition. The yellowness index (YI) of the crude levulinic acid was 104. The sample was dark yellow to amber in color.

116.18 g (0.88 mol) Crude levulinic acid, 45.16 g (0.5 mol) 1,4-butanediol, and 200 ppm camphor sulfonic acid were added to an empty 500 mL, 3-neck round bottom flask equipped with a magnetic stir-bar, Dean-Stark trap and overhead condenser, a thermocouple, and a nitrogen inlet. The contents were heated with an oil bath for 6 hours at 160° C. Volatile condensate was collected in the Dean Stark trap. A sample of the reactor was analyzed by GC-FID and the composition was found to be:

| | |
|---|---|
| 1.25% | un-reacted 1,4-BDO |
| 7.23% | un-reacted levulinic acid |
| 22.2% | LA-BDO-OH |
| 66.8% | LA-BDO-LA product |
| 1.3% | unknown higher molecular weight species |

The product was crystallized by the addition of water to afford white crystals. The yield of product was 61.05 grams and the composition by GC-FID was found to be:

| | |
|---|---|
| 0.13% | 1,4-BDO |
| 0.7% | levulinic acid |
| 3.5% | LA-BDO-OH |
| 95.5% | LA-BDO-LA product |
| 0.02% | unknown higher molecular weight species |

Example 3

Manufacture of Purified LA with Sulfuric Acid Catalyst

This prophetic example details the manufacturing of pure levulinic acid from a diketone-diester. The levulinic acid that can be manufactured by this method is purer than the crude levulinic acid used in the Example 1. It is particularly devoid of high molecular weight oligomers. In this example, the ketocarboxylic ester is decomposed with an acid catalyst to produce the levulinic acid ("ketocarboxylic acid").

LA-BDO-LA (286 g, 1 mol), water (144 g, 8.0 mol), and sulfuric acid (0.5 wt %) are added to an empty 500 mL, 3-neck round bottom flask equipped with a magnetic stir-bar. The contents are heated to reflux for 4 hours. Levulinic acid and 1,4-butanediol are observed in the reaction product composition. The reaction mixture is neutralized with dibasic sodium phosphate and filtered. The water is stripped out of the mixture, and levulinic acid and 1,4-butanediol are distilled into their pure components via vacuum distillation at 5 to 10 Torr. The levulinic acid will have a yellowness index (YI) value of less than 5 units and a purity of greater than 98%. The hydrolysis of the diketone-diester to produce levulinic acid is shown in the reaction scheme below.

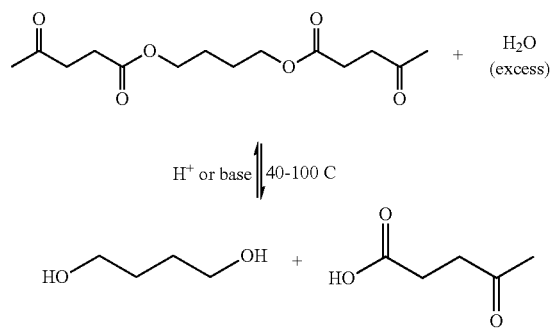

Example 4

Manufacture of LA with a Sodium Hydroxide Base at 80° C.

This prophetic example details the manufacturing of pure levulinic acid from a diketone-diester. The levulinic acid that can be manufactured by this method is purer than the crude levulinic acid used in the Example 1 or 2. In this example, the ketocarboxylic ester is saponified with a base to produce the ketocarboxylic acid.

LA-BDO-LA (286 g, 1.0 mol), water (72 g, 4.0 mol), and sodium hydroxide (8 g, 0.2 mol) are added to an empty 500 mL, 3-neck round bottom flask equipped with a magnetic stir-bar. The contents are heated to 80° C. for 4 hours. Sodium levulinate and 1,4-butanediol are observed in the reaction product composition. Sodium hydroxide is added to precipitate the sodium levulinate salt from the reaction mixture. The sodium levulinate is filtered away from the 1,4-butanediol and re-acidified with 10% sulfuric acid to form levulinic acid and sodium sulfate. The levulinic acid is stripped of water, the sodium sulfate is filtered, and the levulinic acid is distilled under vacuum at 1 to 5 Torr. The levulinic acid has a YI value of less than 5 units and a purity of greater than 99%.

Example 5

Manufacture of LA with a Sodium Hydroxide Base at 60° C.

This prophetic example details the manufacturing of pure levulinic acid from a diketone-diester. The levulinic acid that can be manufactured by this method is purer than the crude levulinic acid used in the Example 1 or 2. In this example, the ketocarboxylic ester is saponified with a base to produce the ketocarboxylic acid.

LA-BDO-LA (286 g, 1.0 mol), water (72 g, 4.0 mol), and sodium hydroxide (80 g, 2.0 mol) are added to an empty 1 L, 3-neck round bottom flask equipped with a magnetic stir-bar. The contents are heated to 60° C. for 4 hours. Levulinic acid and 1,4-butanediol are observed in the reaction product composition. The sodium levulinate is filtered away from the 1,4-butanediol and re-acidified with 10% sulfuric acid to form levulinic acid and sodium sulfate. The levulinic acid is stripped of water, the sodium sulfate is filtered, and the levulinic acid is distilled under vacuum at 5 to 10 Torr. The levulinic acid has a YI value of less than 5 units and a purity of greater than 99%.

Example 6

LA-BDO-LA

A crude levulinic acid composition comprising 14.9 g (0.128 mol) levulinic acid, 0.449 g (9.76×10$^{-3}$ mol) formic acid, 30 g (1.66 mol) deionized (DI) water, and 2.24 mL concentrated sulfuric acid was esterified with 2.89 g (3.21×10$^{-2}$ mol) 1,4-butanediol. The flask was flushed with $N_2$ gas for 10 minutes before placing in an oil bath at room temperature. The flask was then evacuated to 300 Torr before heating to 105° C. The reaction was held at 105° C. for 60 minutes before increasing the temperature to 115° C. for 25 minutes. Finally, the pressure was decreased to 150 Torr with the temperature being held at 115° C. for an additional 25 minutes, at which point the flask was cooled to room temperature under vacuum before backfilling with $N_2$. GC-FID analysis showed a peak in the chromatogram that corresponded to LA-BDO-LA.

Example 7

LA-PDO-LA

The crude levulinic acid composition described in Example 6 is esterified with 2.434 g (3.21×10$^{-2}$ mol) 1,3-propanediol. The procedure of Example 6 is followed, and GC-FID analysis shows a peak corresponding to LA-PDO-LA.

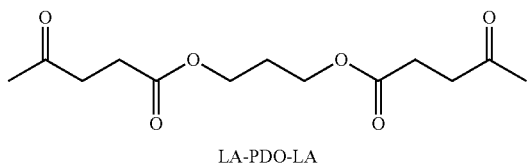 [SMILES: CC(=O)CCC(=O)OCCCOC(=O)CCC(C)=O]

LA-PDO-LA

Example 8

LA-TMP-LA

The crude levulinic acid composition described in Example 6 is esterified with 3.44 g (2.6×10$^{-2}$ mol) trimethylolpropane (TMP). The procedure of Example 6 is followed, and GC-FID analysis shows a peak corresponding to the tris ketone LA-TMP-LA.

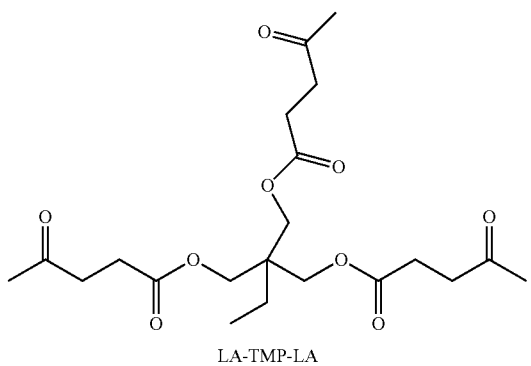 [SMILES: CCC(COC(=O)CCC(C)=O)(COC(=O)CCC(C)=O)COC(=O)CCC(C)=O]

LA-TMP-LA

Example 9

LA-BDO-LA, Camphor Sulfonic Acid Catalyst

A crude levulinic acid composition comprising 14.9 g (0.128 mol) levulinic acid, 0.449 g (9.76×10$^{-3}$ mol) formic acid, 30 g (1.66 mol) DI water, and 0.3484 g (1.50×10$^{-3}$ mol) camphor sulfonic acid was esterified with 2.89 g (3.21×10$^{-2}$ mol) 1,4-butanediol. The procedure for Example 6 was followed, and analysis of the reaction mixture by GC-FID showed a peak corresponding to LA-BDO-LA.

Example 10

LA-BDO-LA, Amberlyst® 35 Catalyst

A crude levulinic acid composition comprising 14.9 g (0.128 mol) levulinic acid, 0.449 g (9.76×10$^{-3}$ mol) formic acid, and 30 g (1.66 mol) DI water was esterified with 2.89 g (3.21×10$^{-2}$ mol) 1,4-butanediol in the presence of a slurry of 0.0956 g Amberlyst® 35 (Dow Chemical Company). The procedure for Example 6 was followed, and analysis of the reaction mixture by GC-FID showed a peak corresponding to LA-BDO-LA.

Example 11

Extraction of LA-BDO-LA into Toluene

A scintillation vial was charged with an approximately equal mass of LA-BDO-LA (prepared according to Example 6) and toluene. The solution was agitated by hand until the mixture was homogeneous, at which point the vial was loosely capped and allowed to sit at room temperature. After 12 hours, LA-BDO-LA crystals were observed in the vial. GC-FID analysis of the crystals was found to be:

| | |
|---|---|
| 98.5% | LA-BDO-LA |
| 1.5% | unknown impurity |

Example 12

AA-BDO-AA

A crude acetoacetic acid composition comprising 14.6 g (0.130 mol) acetoacetic acid and 30 g (1.66 mol) DI water is esterified with 2.89 g ($3.21 \times 10^{-2}$ mol) 1,4-butanediol in the presence of 2.24 mL concentrated sulfuric acid. The procedure for Example 6 is followed, and analysis of the reaction mixture by GC-FID shows a peak corresponding to AA-BDO-AA.

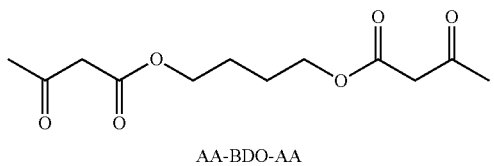

AA-BDO-AA

Example 13

PA-BDO-PA

A crude pyruvic acid composition comprising 12.6 g (0.130 mol) pyruvic acid, and 30 g (1.66 mol) DI water is esterified with 2.89 g ($3.21 \times 10^{-2}$ mol) 1,4-butanediol in the presence of 2.24 mL concentrated sulfuric acid. The procedure for Example 6 is followed, and analysis of the reaction mixture by GC-FID shows a peak corresponding to PA-BDO-PA.

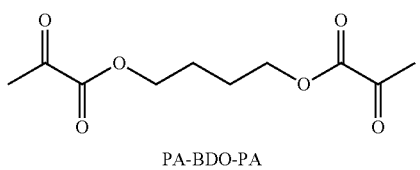 [SMILES: CC(=O)C(=O)OCCCCOC(=O)C(C)=O ; "PA-BDO-PA"]

PA-BDO-PA

Example 14

LA-BDO-LA, MIBK Extracted, Camphorsulfonic Acid

The crude LA mixture from Example 6 was extracted using methyl isobutyl ketone (MIBK), yielding a solution comprising approximately 1% levulinic acid with various unidentified impurities in MIBK. The extracted solution exhibited a pH near 6. A 3 neck round bottom flask equipped with stirring, a Dean-Stark trap and condenser was charged with 11.2 g of the aforementioned solution and 0.0456 g ($5.06 \times 10^{-4}$ mol) 1,4-butanediol. The reaction was allowed to stir for 10 minutes under flowing $N_2$ before the addition of 5.6 microliters of concentrated sulfuric acid. The reaction was stirred for 5 minutes under $N_2$ before being evacuated to 300 Torr and heated to 105° C. for 60 minutes. After 60 minutes, the temperature was increased to 115° C. for 25 minutes before decreasing the pressure of the reactor to 150 Torr while holding at 115° C. for an additional 25 minutes. After cooling to room temperature under vacuum, the reactor was backfilled with $N_2$ and sampled for GC-FID analysis. This analysis showed a peak consistent with LA-BDO-LA corresponding to 5% (peak area) of the total chromatograph.

Example 15

LA-BDO-LA, Hydrolysate

To a dry 3 neck round bottom flask equipped with a magnetic stir bar, a Dean-Stark trap and a reflux condenser was added: 1) 10.0062 g of a composition comprising: approximately 8.3 g (19 wt %) levulinic acid, 0.4 g (1 wt %) formic acid, 2.24 mL (9 wt %) concentrated sulfuric acid, 2) 30 g (70 wt %) water; and 3) 0.1082 g ($1.20 \times 10^{-3}$ mol) 1,4-butanediol. The reaction mixture was stirred under flowing $N_2$ for 30 minutes before the addition of 0.313 g ($3.73 \times 10^{-3}$ mol) sodium bicarbonate. The reaction was again allowed to stir for 20 min at room temperature under $N_2$ before evacuating to 300 Torr and heating. The reaction was heated to 105° C. for 60 minutes at 300 Torr, at which time the temperature was increased to 115° C. for an additional 25 minutes. The reactor pressure was next reduced to 150 Torr while maintaining the temperature at 115° C. for an additional 25 minutes. After cooling to room temperature under vacuum, the reactor was backfilled with $N_2$ and sampled for GC-FID analysis. This analysis showed a peak consistent with LA-BDO-LA corresponding to approximately 1% (peak area) of the total chromatograph.

Example 17

LA from LA-BDO-LA by Saponification using Sodium Hydroxide

To a 100 mL round bottom flask equipped with a stir bar was added 4.990 g LA-BDO-LA prepared according to Example 16 and recrystallized twice to greater than 99% purity by GC-FID. To this was added a solution of 0.88 g NaOH in 4.46 g $H_2O$. The reaction mixture was then stirred at 80° C. for 210 minutes, at which point the reaction was cooled and the pH adjusted to approximately 4.5, according to the procedure described in Example 19. GC-FID analysis showed the complete disappearance of starting material and the appearance of peaks attributed to LA and 1,4-BDO, indicating near quantitative hydrolysis of the diester.

Example 18

LA from LA-BDO-LA Via Hydrolysis with Sulfuric Acid

To a 100 mL round bottom flask with a stir bar is charged with 4.990 g LA-BDO-LA prepared from pure LA and recrystallized twice. To this is added a solution of 10 grams of 5 wt % weight sulfuric acid. The reaction mixture is then stirred at reflux until completion, as determined by GC-FID analysis of the mixture.

Example 19

LA from Hydrolysis of LA-BDO-LA by Aqueous Hydrochloric Acid

To a 100 mL round bottom flask containing the hydrolysis mixture prepared in Example 17 is added a 0.1 N $HCl_{(aq)}$ solution dropwise until a pH of 4.5 is obtained.

Example 20

Hydrolysis of LA-BDO-LA with Aqueous Sodium Hydroxide

To a 100 mL round bottom flask containing the hydrolysis mixture prepared in Example 18 is added a 10% $NaOH_{(aq)}$ solution dropwise until a pH of 4.5 is obtained.

Example 21

Distillation of 1,4-butanediol from Levulinic Acid

To a 250 mL round bottom flask with a magnetic stir bar is added 100 mL of an aqueous hydrolysis mixture containing 2 equivalents levulinic acid and 1 equivalent 1,4-butandiol. The round bottom flask is assembled on a distillation apparatus containing a distillation column leading to a jacketed condenser, with a tared receiving flask for the distillate. The distillation apparatus is first evacuated to 25 Torr and subsequently heated to no higher than 125° C. to ensure distillation of only the 1,4-butanediol. The LA remaining in the 250 mL round bottom flask can be isolated and transferred into permanent storage or purified.

Example 22

LA, Distillation of

The LA from Example 21 is distilled overhead by a falling film evaporator to afford LA with a solution YI less than 5.

Example 23

LA, Recrystallization of

The LA from Example 22 is recrystallized in the melt to afford greater than 99% purity and a solution YI of less than 5.

From the aforementioned examples, it can be seen that pure levulinic acid can be produced from crude levulinic acid that contains a higher percentage of impurities. The pure levulinic acid contains less than 2 wt % impurities, specifically less than 1 wt % impurities, and more specifically less than 0.05 wt % impurities, based on the total weight of the levulinic acid.

As used herein, the singular forms "a," "an," and "the" are intended to include the plural forms as well, unless the context clearly indicates otherwise. The term "or" means "and/or." The endpoints of all ranges directed to the same component or property are inclusive of the endpoint and independently combinable, except when the modifier "between" is used. The modifier "about" used in connection with a quantity is inclusive of the stated value and has the meaning dictated by the context (e.g., includes the degree of error associated with measurement of the particular quantity). A "combination" is inclusive of blends, mixtures, alloys, reaction products, and the like.

In general, the compositions or methods can alternatively comprise, consist of, or consist essentially of, any appropriate components or steps disclosed. The compositions can additionally, or alternatively, be formulated so as to be devoid, or substantially free, of any components, materials, ingredients, adjuvants, or species, or steps used in the prior art compositions or that are otherwise not necessary to the achievement of the function and/or objectives of the present claims.

Unless otherwise defined, all terms (including technical and scientific terms) used have the same meaning as commonly understood by one of ordinary skill in the art to which this invention belongs. Compounds are described using standard nomenclature. Any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group. "Alkyl" means a straight or branched chain saturated aliphatic hydrocarbon having the specified number of carbon atoms. "Alkylene" means a straight or branched divalent aliphatic hydrocarbon group having the specified number of carbon atoms. "Aryl" means a cyclic moiety in which all ring members are carbon and a ring is aromatic. More than one ring can be present, and any additional rings can be independently aromatic, saturated or partially unsaturated, and can be fused, pendant, spirocyclic or a combination thereof.

A "hydrocarbon group" as used herein means a group having the specified number of carbon atoms and the appropriate valence in view of the number of substitutions shown in the structure. Hydrocarbon groups contain at least carbon and hydrogen, and can optionally contain 1 or more (e.g., 1-8) heteroatoms selected from N, O, S, Si, P, or a combination comprising at least one of the foregoing. Hydrocarbon groups can be unsubstituted or substituted with one or more substituent groups up to the valence allowed by the hydrocarbyl group independently selected from a $C_{1-30}$ alkyl, $C_{2-30}$ alkenyl, $C_{2-30}$ alkynyl, $C_{6-30}$ aryl, $C_{7-30}$ arylalkyl, $C_{1-12}$ alkoxy, $C_{1-30}$ heteroalkyl, $C_{3-30}$ heteroarylalkyl, $C_{3-30}$ cycloalkyl, $C_{3-15}$ cycloalkenyl, $C_{6-30}$ cycloalkynyl, $C_{2-30}$ heterocycloalkyl, halogen (F, Cl, Br, or I), hydroxy, nitro, cyano, amino, azido, amidino, hydrazino, hydrazono, carbonyl, carbamyl, thiol, carboxy ($C_{1-6}$alkyl) ester, carboxylic acid, carboxylic acid salt, sulfonic acid or a salt thereof, and phosphoric acid or a salt thereof.

While stereochemistry of the various compounds is not explicitly shown, it is to be understood that this disclosure encompasses all isomers.

All cited patents, patent applications, and other references are incorporated by reference in their entirety.

While the invention has been described with reference to exemplary embodiments, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for reducing a content of an impurity in a ketocarboxylic acid composition comprising at least 1 wt % of the impurity and a ketocarboxylic acid I

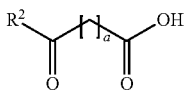

wherein
$R^2$ is $C_1$-$C_6$ alkyl and
a=0-3,
the method comprising:
contacting a hydrocarbon polyol II G-[OH]$_t$  II wherein
G is a hydrocarbyl group having a valence of t, and
t=2-3,
with the ketocarboxylic acid composition in an esterification reaction mixture wherein the ketocarboxylic acid I is present in an amount of at least 0.75 equivalents of the ketocarboxylic acid I per one equivalent of hydroxy group in the hydrocarbon polyol II, under conditions effective to form a ketocarboxylic ester III

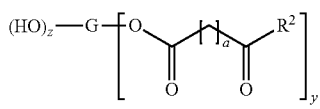

wherein
$R^2$ is $C_1$-$C_6$ alkyl,
a=0-3,
y=2-3 and z=0-1, provided that z+y=t; and
isolating the ketocarboxylic ester III from the esterification reaction mixture.

2. The method of claim 1, wherein G is a $C_2$-$C_{32}$ hydrocarbon containing 1 or more straight chain, branched or cyclic groups that can be saturated, unsaturated, aromatic, or substituted with up to 12 ether oxygens.

3. The method of claim 1, wherein
G is a $C_2$-$C_{12}$ alkylene optionally substituted with up to 5 ether oxygens, $C_5$-$C_8$ cycloalkylene, or $C_6$-$C_{12}$ arylene;
$R^2$ is $C_1$-$C_6$ alkyl,
a=0-3,
y=2-3, and
z=0.

4. The method of claim 1, wherein
G is a $C_2$-$C_{12}$ alkylene optionally substituted with up to 5 ether oxygens,
$R^2$ is $C_1$-$C_3$ alkyl,
a=1-2,
y=2, and
z=0.

5. The method of claim 1, wherein
G is a $C_2$-$C_6$ alkylene
$R^2$ is methyl,
a=1-2,
y=2, and
z=0.

6. The method of claim 1, wherein
G is ethylene, n-propylene, n-butylene, or n-hexylene,
$R^2$ is methyl,
a=2, and
y=2, and
z=0.

7. The method of claim 1, wherein the esterification is conducted in the presence of an esterification catalyst comprising a Brønsted-Lowry acid, a Lewis acid, or a combination comprising at least one of the foregoing catalysts.

8. The method of claim 1, wherein the esterification is conducted in the presence of a catalyst comprising sulfuric acid, arylsulfonic acid, a hydrate of an aryl sulfonic acid, p-toluenesulfonic acid monohydrate, methane sulfonic acid, camphor sulfonic acid, dodecyl benzene sulfonic acid, perchloric acid, hydrobromic acid, titanium tetraalkoxides, aluminum trialkoxides, tin(II) alkoxides, carboxylates, organo-tin alkoxides, organo-tin carboxylates, boron trifluoride, hydrochloric acid, or a combination comprising at least one of the foregoing catalysts.

9. The method of claim 7, wherein the esterification catalyst is a heterogeneous acid catalyst.

10. The method of claim 1, wherein the esterification is conducted at a temperature of about 80 to about 250° C.

11. The method of claim 1, wherein the esterification is conducted in an inert gas atmosphere or at a sub-atmospheric pressure.

12. The method of claim 1, wherein water is removed from the esterification reaction mixture during at least a portion of the contacting.

13. The method of claim 12, wherein G is n-butylene, and there is less than or equal to a 10 weight percent loss of 1,4-butanediol as tetrahydrofuran when the water is removed from the reaction mixture.

14. The method of claim 1, wherein the isolating is by washing, crystallizing, filtering, liquid-liquid phase separating, precipitation, or a combination of at least one of the foregoing.

15. The method of claim 1, wherein the isolating comprises crystallizing the ketocarboxylic ester III from the esterification reaction mixture.

16. The method of claim 15, wherein
G is ethylene, n-propylene, n-butylene, or n-hexylene,
$R^2$ is methyl,
a=2,
y=2, and
z=0.

17. The method of claim 15, wherein the isolating further comprises washing the crystallized ketocarboxylic ester III with water.

18. The method of claim 17, wherein the washing removes color-bodies, acid catalyst, unreacted ketocarboxylic acid, or a combination comprising at least one of the foregoing.

19. The method of claim 1, wherein the ketocarboxylic acid composition comprises at least 1 wt % of the impurity, and the separated ketocarboxylic ester III comprises less than 1 wt % of the impurity.

20. The method of claim 1, wherein the ketocarboxylic acid composition comprises at least 10 wt % of the impurity, and the separated ketocarboxylic ester III comprises less than 1 wt % of the impurity.

21. The method of claim 1, wherein the ketocarboxylic acid composition comprises at least 5% water.

22. The method of claim 1, wherein the impurity in the ketocarboxylic acid composition comprises a residue of a biomass.

23. The method of claim 1, wherein the impurity comprises furfural, formic acid, furfuryl alcohol, hydroxymethyl furfural, angelica lactone, acetic acid, methanol, a humin, a polysaccharide, a saccharide, or a combination comprising at least one of the foregoing impurities.

24. The method of claim 1, further comprising decomposing the isolated ketocarboxylic ester III to provide the ketocarboxylic acid I or a salt thereof.

25. The method of claim 24, wherein decomposing is by hydrolysis with acid or saponification with base.

26. The method of claim 24, wherein the decomposing is conducted at a temperature of about 40 to about 150° C.

27. The method of claim 25, wherein the acid is a mineral acid.

28. The method of claim 27, wherein the mineral acid is sulfuric acid or hydrochloric acid.

29. The method of claim 24, wherein the base is a quaternary ammonium hydroxide, a tetramethyl ammonium hydroxide, a tetraethyl ammonium hydroxide, a tetrapropyl ammonium hydroxide, a tetrabutyl ammonium hydroxide, a tetraoctyl ammonium hydroxide, an alkali metal hydroxide, an alkaline earth metal hydroxide, a lithium hydroxide, a sodium hydroxide, a potassium hydroxide, a magnesium hydroxide, a calcium hydroxide, a lithium alkoxide, a sodium alkoxide, a potassium alkoxide, a lithium methoxide, a lithium ethoxide, a lithium butoxide, a sodium methoxide, a sodium ethoxide, a sodium butoxide, a potassium methoxide, a potassium ethoxide, a potassium butoxide or a combination comprising at least one of the foregoing bases.

30. The method of claim 1, further comprising distilling the hydrocarbon polyol during the decomposing, after the decomposing, or a combination thereof.

31. The method of claim 1, further comprising filtering the ketocarboxylic acid and the hydrocarbon polyol after the decomposing.

32. The method of claim 1, further comprising neutralizing any un-neutralized acid catalyst after the decomposing.

33. The method of claim 1, further comprising precipitating the ketocarboxylate salt after the decomposing.

34. The method of claim 30, wherein there is less than or equal to a 20 weight percent loss of 1,4-butanediol as tetrahydrofuran in water removed during the distilling.

35. A method for the purification of a composition comprising ketocarboxylic acid I and an impurity,

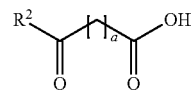

wherein
   $R^2$ is $C_1$-$C_6$ alkyl and
   a=0-3,
the method comprising:
   esterifying a hydrocarbon polyol II with a composition comprising a ketocarboxylic acid I and an impurity in an esterification reaction mixture, wherein the ketocarboxylic acid I is present in an amount of at least 0.75 equivalents of the ketocarboxylic acid I per one equivalent of hydroxy group in the hydrocarbon polyol II G-[OH]$_t$     II wherein
   G is ethylene, n-propylene, n-butylene, or n-hexylene, and
   t=2,
to form a ketocarboxylic ester III

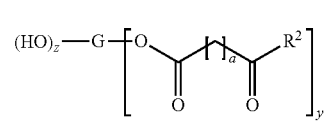

wherein
   $R^2$ is $C_1$-$C_6$ alkyl,
   a=0-3,
   y=2-3 and z=0-1, provided that z+y=t;
isolating the polyketocarboxy ester III from the esterification reaction mixture, and decomposing the isolated polyketocarboxylic acid ester III to provide the purified ketocarboxylic acid I composition or a salt thereof.

* * * * *